US011464490B2

(12) United States Patent
Luo et al.

(10) Patent No.: US 11,464,490 B2
(45) Date of Patent: Oct. 11, 2022

(54) REAL-TIME FEEDBACK AND SEMANTIC-RICH GUIDANCE ON QUALITY ULTRASOUND IMAGE ACQUISITION

(71) Applicant: Verathon Inc., Bothell, WA (US)

(72) Inventors: Si Luo, Bothell, WA (US); Dave Scott, Bothell, WA (US)

(73) Assignee: Verathon Inc., Bothell, WA (US)

( * ) Notice: Subject to any disclaimer, the term of this patent is extended or adjusted under 35 U.S.C. 154(b) by 200 days.

(21) Appl. No.: 16/189,134

(22) Filed: Nov. 13, 2018

(65) Prior Publication Data
US 2019/0142390 A1 May 16, 2019

Related U.S. Application Data

(60) Provisional application No. 62/585,665, filed on Nov. 14, 2017.

(51) Int. Cl.
*A61B 8/08* (2006.01)
*A61B 8/00* (2006.01)
(Continued)

(52) U.S. Cl.
CPC ............ *A61B 8/5215* (2013.01); *A61B 8/461* (2013.01); *G06N 3/02* (2013.01); *G06T 7/73* (2017.01);
(Continued)

(58) Field of Classification Search
CPC ........ A61B 8/461; A61B 8/5215; G06N 3/02; G06T 7/73; G16H 30/20; G16H 30/40; G16H 40/60
See application file for complete search history.

(56) References Cited

U.S. PATENT DOCUMENTS 6,749,569 B1 * 6/2004 Pellegretti ........... G01S 7/52074
600/441
7,043,474 B2 5/2006 Mojsilovic et al.
(Continued)

OTHER PUBLICATIONS

Artignan, Xavier et al., "Online ultrasound image guidance for radiotherapy of prostate cancer: impact of image acquisition on prostate displacement" International Journal of Radiation Oncology*Biology*Physics, vol. 48, Issue 2, Jun. 1, 2004, retrieved Feb. 13, 2019, <https://www.sciencedirect.com/science/article/pii/S0360301604002159>.
(Continued)

*Primary Examiner* — Yi-Shan Yang
*Assistant Examiner* — Alexei Bykhovski
(74) *Attorney, Agent, or Firm* — Snyder, Clark, Lesch & Chung, LLP

(57) ABSTRACT

A method for providing real-time feedback and semantic-rich guidance on ultrasound image quality is performed by a processor in an ultrasound system. The method includes receiving an ultrasound image and classifying the ultrasound image into one or more categories based on image features. The classifying creates a classified image. The method also includes determining whether the classified image provides an acceptable representation of a target organ. In response to determining that the classified image does not provide an acceptable representation of the target organ, the method includes selecting operator guidance corresponding to the one or more category; presenting via a display and/or audible sound, the selected operator guidance; and receiving additional ultrasound images. The method further includes calculating a result based on the classified image in response to determining that the classified image provides an acceptable representation of the target organ.

20 Claims, 10 Drawing Sheets

(51) Int. Cl.
*G06N 3/02* (2006.01)
*G06T 7/73* (2017.01)
*G16H 30/20* (2018.01)
*G16H 30/40* (2018.01)
*G16H 40/60* (2018.01)

(52) U.S. Cl.
CPC ............. *G16H 30/20* (2018.01); *G16H 30/40* (2018.01); *G16H 40/60* (2018.01)

(56) References Cited

U.S. PATENT DOCUMENTS

| | | |
|---|---|---|
| 9,157,894 B2 | 10/2015 | Jiang et al. |
| 9,730,675 B2 | 8/2017 | Deng et al. |
| 2004/0122307 A1 | 6/2004 | Rottem |
| 2010/0168571 A1 | 7/2010 | Savery et al. |
| 2010/0298704 A1 | 11/2010 | Pelissier et al. |
| 2012/0065510 A1 | 3/2012 | Snare et al. |
| 2012/0108965 A1 | 5/2012 | Lazebnik |
| 2014/0004488 A1 | 1/2014 | Tepper et al. |
| 2016/0048958 A1* | 2/2016 | Miga ................. A61B 8/483 382/131 |
| 2016/0143627 A1 | 5/2016 | Vignon et al. |
| 2016/0302759 A1* | 10/2016 | Shi ................... A61B 8/4245 |
| 2016/0345931 A1* | 12/2016 | Xu ....................... A61B 8/52 |
| 2017/0086785 A1 | 3/2017 | Bjaerum |
| 2017/0105701 A1 | 4/2017 | Pelissier et al. |
| 2018/0144465 A1* | 5/2018 | Hsieh .................. G06N 3/08 |
| 2018/0275258 A1* | 9/2018 | Pintoffl .............. G01S 7/52046 |

OTHER PUBLICATIONS

International Search Report and Written Opinion issued in corresponding International Application No. PCT/US2018/060695, dated Feb. 21, 2019, 15 pages.

\* cited by examiner

REAL-TIME FEEDBACK AND SEMANTIC-RICH GUIDANCE ON QUALITY ULTRASOUND IMAGE ACQUISITION

CROSS-REFERENCE TO RELATED APPLICATION

This application claims priority under 35 U.S.C. § 119, based on U.S. Provisional Patent Application No. 62/585,665 filed Nov. 14, 2017, the disclosure of which is hereby incorporated by reference.

BACKGROUND OF THE INVENTION

Ultrasound scanners are typically used to identify a target organ or another structure in the body and/or determine features associated with the target organ/structure, such as the size of a structure or the volume of fluid in an organ. Obtaining an adequate quality of ultrasound images can be challenging even for experienced sonographers. For inexperienced users, the challenges to acquire good quality ultrasound images can be even greater, as such users generally lack sufficient training and experience to be able to tell whether an ultrasound image (e.g., as shown in real time on a screen of an ultrasound device) is acceptable.

DETAILED DESCRIPTION OF THE PREFERRED EMBODIMENTS

The following detailed description refers to the accompanying drawings. The same reference numbers in different drawings may identify the same or similar elements.

Implementations described herein relate to providing real-time image quality assessment and on-screen or audible guidance to ultrasound system operators, helping the operators to acquire high-quality ultrasound images that can be used for calculating organ measurements or extracting other clinically useful information. Real-time semantic-rich feedback provides a more user-friendly experience, particularly for general practitioners or inexperienced ultrasound operators.

In one implementation, a method for providing real-time feedback and semantic-rich guidance on ultrasound image quality may be performed by a processor in an ultrasound system. The method may include receiving an ultrasound image and classifying the ultrasound image into one or more categories based on image features. The classifying creates a classified image. The method may also include determining whether the classified image provides an acceptable representation of a target organ. When the classified image does not provide an acceptable representation of the target organ, the method may include selecting operator guidance corresponding to the one or more category; presenting via a display and/or audible sound, the selected operator guidance; and receiving additional ultrasound images. The method may further include calculating a result based on the classified image when the classified image provides an acceptable representation of the target organ.

Figure 1:
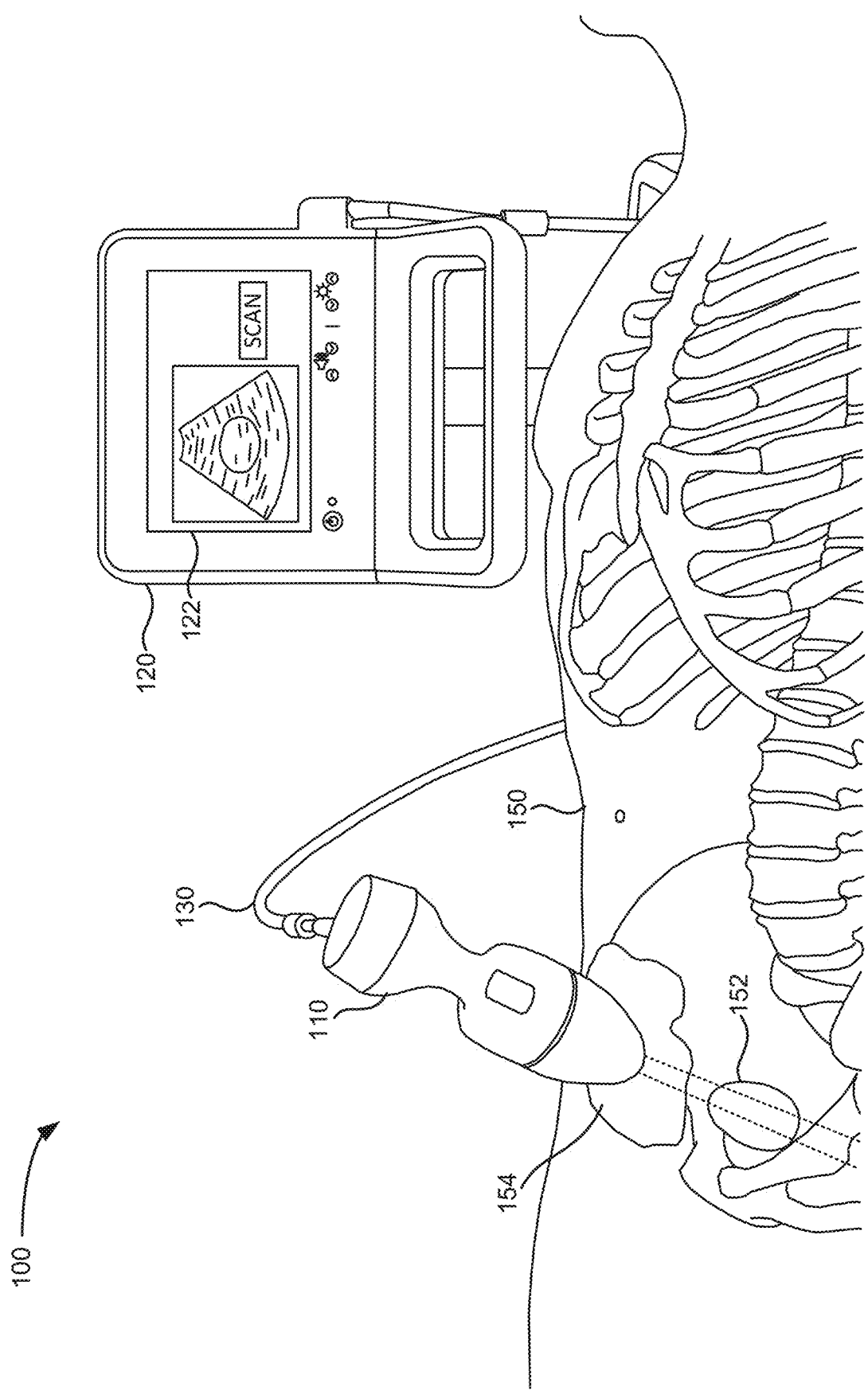
FIG. 1 is a schematic of a scanning system in which systems and methods described herein may be implemented.

FIG. 1 is a schematic of a scanning system 100 in which systems and methods described herein may be implemented. Referring to FIG. 1, scanning system 100 includes a probe 110, a base unit 120, and a cable 130.

Probe 110 includes a handle portion, a trigger, and a nose (or dome) portion. Medical personnel may hold probe 110 via the handle and press the trigger to activate one or more ultrasound transceivers, located in the nose portion, to transmit ultrasound signals toward a target organ of interest. For example, as shown in FIG. 1, probe 110 is located on pelvic area of patient 150 and over a target organ of interest 152, which in this example is the patient's bladder.

The dome of probe 110 is typically formed of a material that provides an appropriate acoustical impedance match to an anatomical portion and/or permits ultrasound energy to be properly focused as it is projected into the anatomical portion. For example, an acoustic gel or gel pads, illustrated at area 154 in FIG. 1, may be applied to patient's skin over the region of interest (ROI) to provide an acoustical impedance match when the dome is placed against the skin.

Probe 110 includes one or more ultrasound transceiver elements and one or more transducer elements within the dome that transmit ultrasound energy outwardly from the dome, and receive acoustic reflections or echoes generated by internal structures/tissue within the anatomical portion. For example, the one or more ultrasound transducer elements may include a one-dimensional, or a two-dimensional array of piezoelectric elements that may be moved within the dome by a motor to provide different scan directions with respect to the transmission of ultrasound signals by the transceiver elements. Alternatively, the transducer elements may be stationary with respect to probe 110 so that the selected anatomical region may be scanned by selectively energizing the elements in the array.

Probe 110 may communicate with base unit 120 via a wired connection, such as via cable 130. In other implementations, probe 110 may communicate with base unit 120 via a wireless connection (e.g., Bluetooth, Wi-Fi, etc.). In each case, base unit 120 includes a display 122 to allow an operator to view processed results from an ultrasound scan, and/or to allow operational interaction with respect to the operator during operation of probe 110. For example, display 122 may include an output display/screen, such as a liquid crystal display (LCD), light emitting diode (LED) based display, or other type of display that provides text and/or image data to an operator. For example, display 122 may provide instructions for positioning probe 110 relative to the selected anatomical portion of patient 150 (such as semantic-rich guidance described further herein). Display 122 may also display two-dimensional or three-dimensional images of the selected anatomical region.

To scan a selected anatomical portion of a patient, the dome of probe 110 may be positioned against a surface portion of patient 150 as illustrated in FIG. 1 that is proximate to the anatomical portion to be scanned. The operator actuates the transceiver and transducer elements, causing the transceiver to transmit ultrasound signals into the body and receive corresponding return echo signals that may be at least partially processed by the transceiver to generate an ultrasound image of the selected anatomical portion. In a particular embodiment, the transceiver transmits ultrasound signals with the center frequency in a range that extends from approximately about two megahertz (MHz) to approximately 10 MHz or more.

In one embodiment, probe 110 may be coupled to a base unit 120 that is configured to generate ultrasound energy at a predetermined frequency and/or pulse repetition rate and to transfer the ultrasound energy to the transceiver. Base unit 120 also includes one or more processors or processing logic configured to process reflected ultrasound energy that is received by the transceiver to produce an image of the scanned anatomical region.

In still another particular embodiment, probe 110 may be a self-contained device that includes one or more microprocessors or processing logic configured within the probe 110 and software associated with the microprocessor to operably control the transceiver and transducer elements, and to process the reflected ultrasound energy to generate the ultrasound image. Accordingly, a display on probe 110 may be used to display the generated image and/or to view semantic-rich feedback and other information associated with the operation of the transceiver. For example, the information may include alphanumeric data that indicates a preferred position of the transceiver prior to performing a series of scans. In other implementations, the transceiver may be coupled to a general-purpose computer, such as a laptop or a desktop computer that includes software that at least partially controls the operation of the transceiver and transducer elements, and also includes software to process information transferred from the transceiver so that an image of the scanned anatomical region may be generated.

Figure 2:
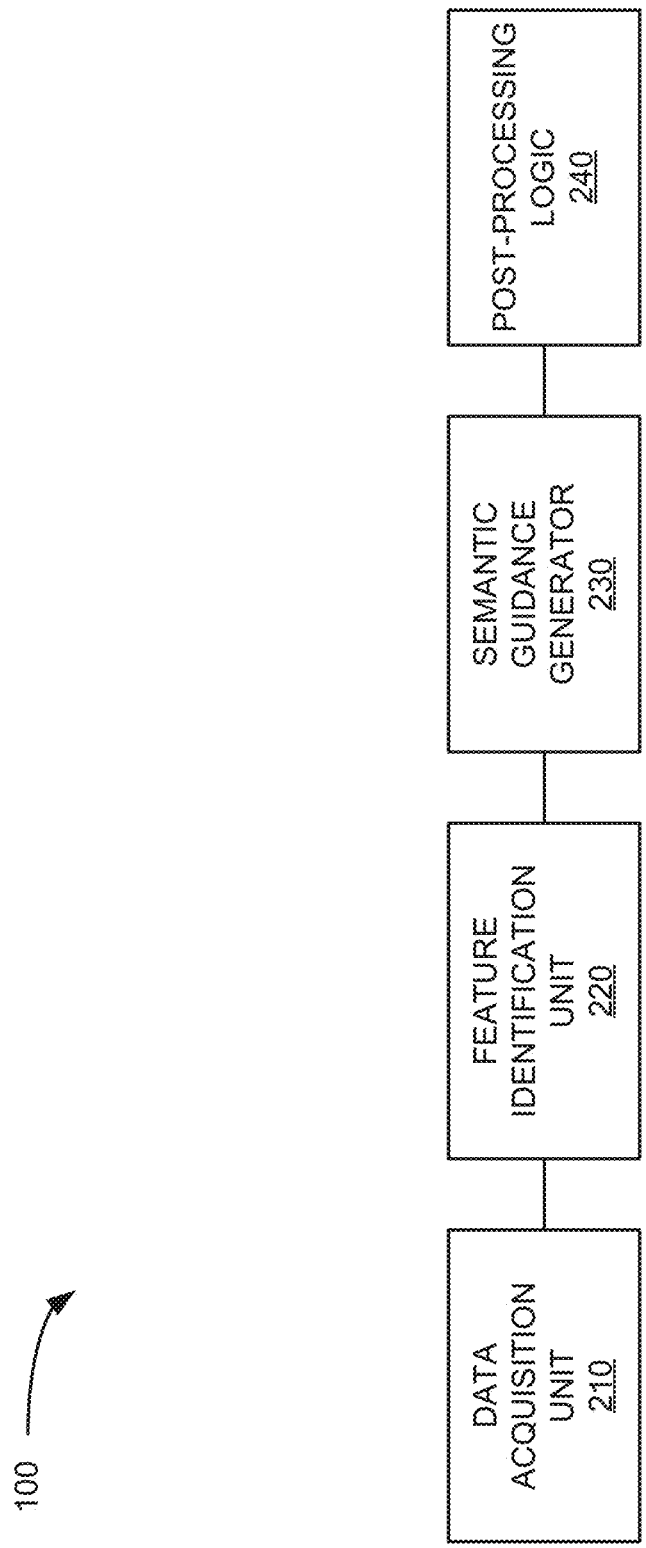
FIG. 2 is a block diagram of functional logic components implemented in the system of FIG. 1 in accordance with an exemplary implementation.

FIG. 2 is a block diagram of functional logic components implemented in system 100 in accordance with an exemplary implementation. Referring to FIG. 2, system 100 includes a data acquisition unit 210, a feature identification unit 220, a semantic guidance generator 230, and post-processing logic 240. In an exemplary implementation, data acquisition unit 210 may be part of probe 110 and the other functional units (e.g., feature identification unit 220, semantic guidance generator 230, and post-processing logic 240) may be implemented in base unit 120. Alternatively, data acquisition unit 210, feature identification unit 220, semantic guidance generator 230, and post-processing logic 240 may be implemented in probe 110. In other implementations, the particular units and/or logic may be implemented by other devices, such as via computing devices or servers located externally with respect to both probe 110 and base unit 120 (e.g., accessible via a wireless connection to the Internet or to a local area network within a hospital, etc.). For example, probe 110 may transmit echo data and/or image data to a processing system via, for example, a wireless connection (e.g., Wi-Fi or some other wireless protocol/technology) that is located remotely from probe 110 and base unit 120.

Figure 3B:
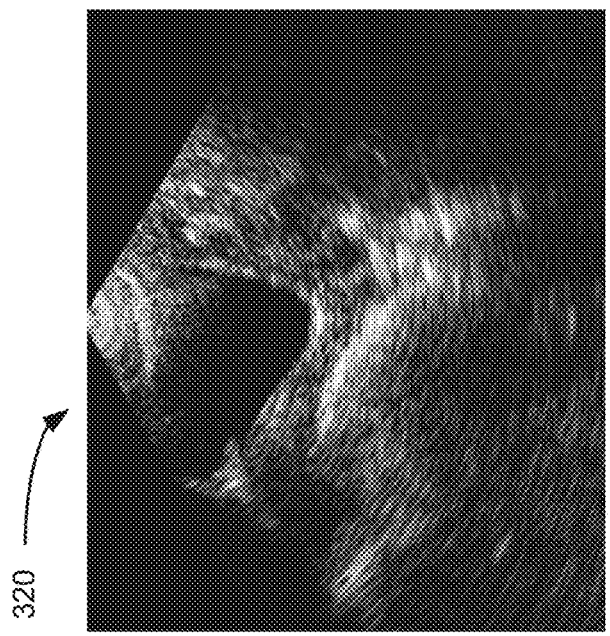
FIG. 3B is a sample image that may be generated by the data acquisition unit of FIG. 2.
Figure 3A:
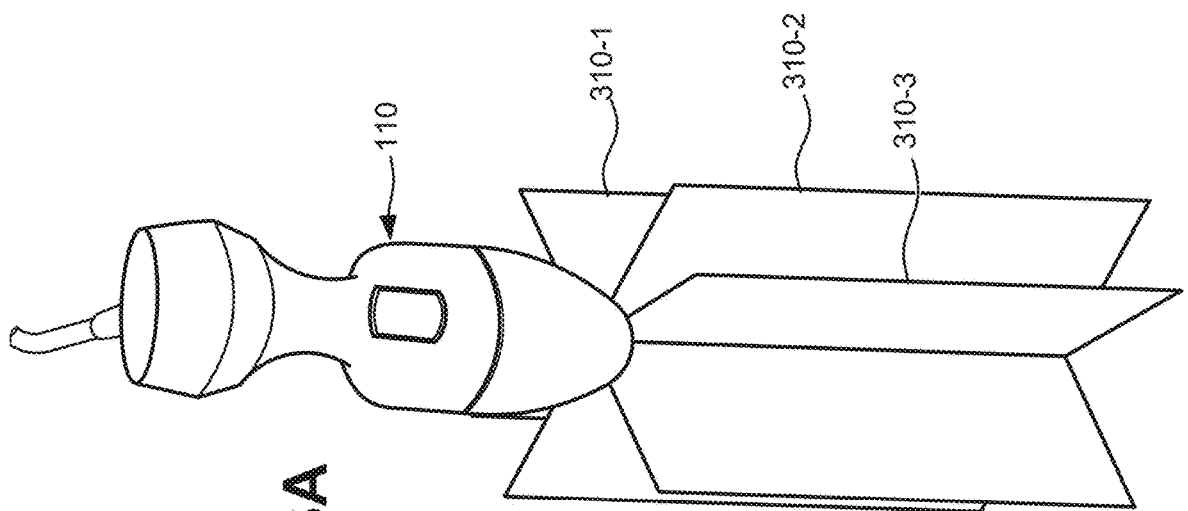
FIG. 3A is a schematic illustrating exemplary scanning planes of the ultrasound probe of FIG. 1.

As described above, probe 110 may include a transceiver that produces ultrasound signals, receives echoes from the transmitted signals and generates B-mode image data based on the received echoes. Data acquisition unit 210 may include, for example, demodulation, decimation, log compression, and filtering sub-modules, to generate an image that can be presented for visualization by a human. A rotating transducer or transducer array with probe 110 may scan along multiple scan planes. FIG. 3A provides a simplified illustration of three scan planes 310-1, 310-2, and 310-3 which may be employed by probe 110 to capture ultrasound images. While three scan planes are shown in FIG. 3A, in practice, more scan planes 310 are used to compile a comprehensive image of a target object. For example, dozens of scan planes may be used by some probes 110. In an exemplary implementation, data acquisition unit 210 obtains data associated with multiple scan planes corresponding to the region of interest in patient 150.

Probe 110 may receive echo data that is processed by data acquisition unit 210 to generate two-dimensional (2-D) B-mode image data to determine information about a target organ, such as bladder size and/or volume. FIG. 3B illustrates a sample image 320 that may be generated by data acquisition unit 210. Image 320 may correspond to echo data from one of scan planes 310 of FIG. 3A. In other implementations, probe 110 may receive echo data that is processed to generate three-dimensional (3D) image data that can be used to determine bladder size and/or volume.

Referring again to FIG. 2, feature identification unit 220 may perform pre-processing of an image (e.g., image 320) and detect in real time if flaws or errors indicative of an improper position or condition of probe 110 are present. For example, feature identification unit 220 may receive an input image (e.g., image 320) from data acquisition unit 210 and detect features in the input image that are indicative of typical probe operator errors (e.g., improper aim, insufficient gel at probe/skin interface, objects interfering with view of target organ, etc.). As described further herein, feature identification unit 220 may analyze image 320 using a multi-class image categorization algorithm to classify the image into one or more of multiple different categories, e.g., image with good quality, image with strong shadows, image with reverberations etc. Feature identification unit 220 is described further, for example, in connection with FIG. 4.

Semantic guidance generator 230 may associate classified images received from feature identification unit 220 with guidance that provides instructions for users to improve aiming of probe 110. For example, based on a category assigned to image 320, semantic guidance generator 230 may generate the semantic-rich guidance. Semantic-rich guidance may include an image feature identification and, if needed, a corrective operator action, e.g., "The image looks great," "Shadow detected—Adjust the probed to avoid the pubic bone," "Reverberation detected—Please apply more gel," "Bladder cropped—Please move the probe location to cover the entire bladder," "Shadow detected—Please adjust the probe angle until the shadow warning signal disappears," etc. The guidance may be displayed on display 122 or provided audibly by a speaker (e.g., in base unit 120) to provide the operator the real-time feedback in helping to acquire quality image data and subsequently accurate volume measurements. In another implementation, the bounding boxes or some form of indictor may also be shown on display 122 to provide the location of detected features.

Post-processing logic 240 may provide additional analysis of an organ, such as cavity-type recognition, volume estimations, or other clinically useful information with B-mode images acquired by data acquisition unit 210. For example, post-processing logic 240 may identify a cavity as a bladder and/or estimate a volume for the bladder.

The exemplary configuration illustrated in FIG. 1 is provided for simplicity. System 100 may include more or fewer logic units/devices than illustrated in FIGS. 1 and 2. For example, system 100 may include multiple data acquisition units 210 and multiple processing units that process the received data. In addition, system 100 may include additional elements, such as communication interfaces (e.g., radio frequency transceivers) that transmit and receive information via external networks to aid in analyzing ultrasound signals to identify a target organ of interest. Furthermore, while illustrations and descriptions herein primarily refer to bladder applications, other embodiments can be applied to wall boundary detection of other organs, such as a prostate/kidney boundary, blood vessels (including aorta), thyroid, etc.

Figure 4:
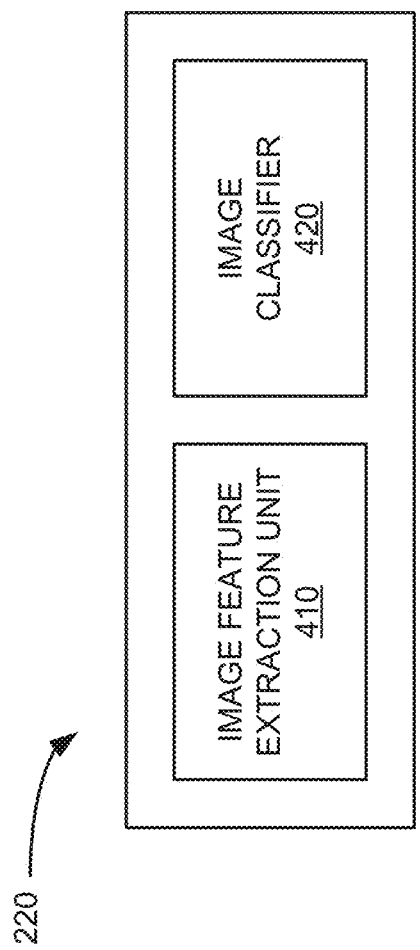
FIG. 4 is a block diagram of functional logic components of the feature identification unit of FIG. 2.

FIG. 4 is a block diagram of functional logic components of feature identification unit 220. As shown in FIG. 4, feature identification unit 220 may include an image feature set extraction unit 410 and an image classifier 420. The functional logic components of FIG. 4 are shown as separate components for descriptive purposes. In other implementations, image feature set extraction unit 410 and an image classifier 420 may be included in a single functional logic components, such as an end-to-end neural network that performs feature extraction and image classification.

Image feature extraction unit 410 may include various set of linear and/or nonlinear mathematical operations to be performed on an image. Image feature extraction unit 410 may be trained by serval sets of training images, where each set of training images includes a certain type of pre-identified feature. Pre-identified features may include, for example, well-identified organs, strong shadows (e.g., typically caused by pubic bone interference), cropped organ boundaries (e.g., due to incorrect probe 110 aiming), reverberations (e.g., due to an inadequate gel 154 coupling at a region of interest), no organ detected (e.g., an air scan), bowel gas interference (e.g., rendering some or all of an underlying organ 152 invisible), etc.

Image classifier 420 may perform multi-class image categorizations of real-time images received from data acquisition unit 210. In one implementation, image classifier 420 may use a multi-class categorization algorithm to classify each incoming ultrasound image during scanning into a specific class/category. In one implementation, image classifier 420 may apply a pre-trained deep convolutional neural network (DCNN). In one implementation, DCNN or other image classification algorithms are well-suited for application of hardwired circuitry, such as a field-programmable gate array (FPGA), an application specific integrated circuits (ASIC), etc., to provide rapid image classification. In one implementation, an input ultrasound image from data acquisition unit 210 is fed into a pre-trained DCNN, where the salient image features are extracted from the input image via several layers of convolution operations. The extracted image features are then fed into fully-connected layers for the classification. The classification results can be presented at the last layer of the neural network, where the category is assigned to the input image as the classifier with a high probability.

Image classifier 420 may support any number of categories for output, as long as the amount of ultrasound images in the training dataset supports each category. However, as the total number of categories grows, the classification distance (e.g., in terms of image feature space) between two categories could be potentially decreased, which could lead to difficulties for the correct classification and the confusion to human operators. In one implementation, image classifier 420 may use no more than twelve categories. Examples of categories identified by image classifier 420 include "strong shadow," "air scan," "lack of gel" (or "reverberation"), "cropped image," "bowel gas interference," and "good image." According to one implementation, image classifier 420 may identify multiple different features/categories for an image received from data acquisition unit 210.

Figure 5:
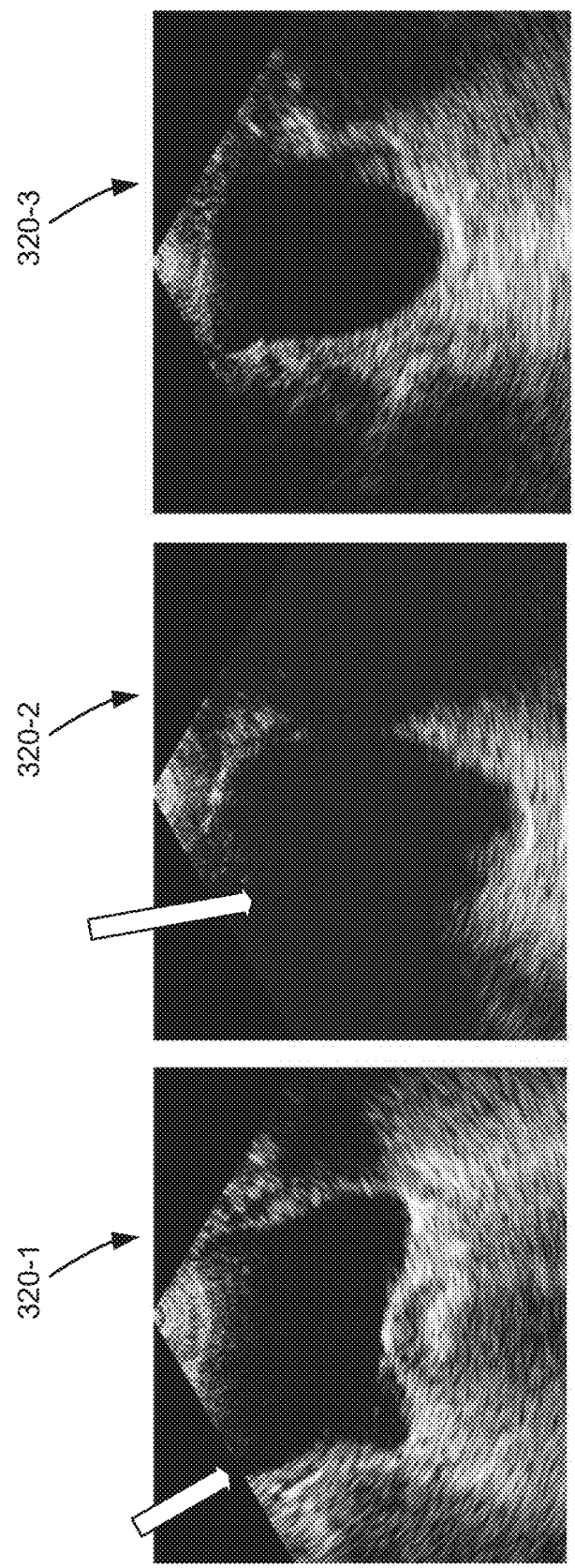
FIGS. 5A-5C are illustrations of ultrasound images with cropped features, strong shadows, and proper orientation, respectively.

FIGS. 5A-5C are sample ultrasound images with features that may be identified by image classifier 420. FIG. 5A illustrates an image 320-1 in which a portion of an organ (e.g., a bladder) is cropped. More particularly, image 320-1 shows an organ wall boundary that exceeds the extents of the ultrasound scan, which makes a discontinuity in the wall of the bladder in image 320-1, as illustrated by the arrow in FIG. 5A. FIG. 5B illustrates an image 320-2 in which a strong shadows prevent detection of an organ wall, as illustrated by the arrow in FIG. 5B. The anatomical information in the shadowed region is, thus, unavailable for calculating results, such as size or volume estimates. FIG. 5C illustrates an image 320-3 where proper probe 110 position/aiming provides acceptable organ detection. For example, in FIG. 5C a complete, uninterrupted bladder wall can be detected in image 320-3. Using DCNN, for example, image classifier 420 may detect identifiable error features such as those in FIGS. 5A-5B and associate respective images 320 with a corresponding error category. Additionally, or alternatively, image classifier 420 may detect acceptable features (or no identifiable error features), such as those in FIG. 5C, and associate respective images 320 with a corresponding good category.

Figure 6:
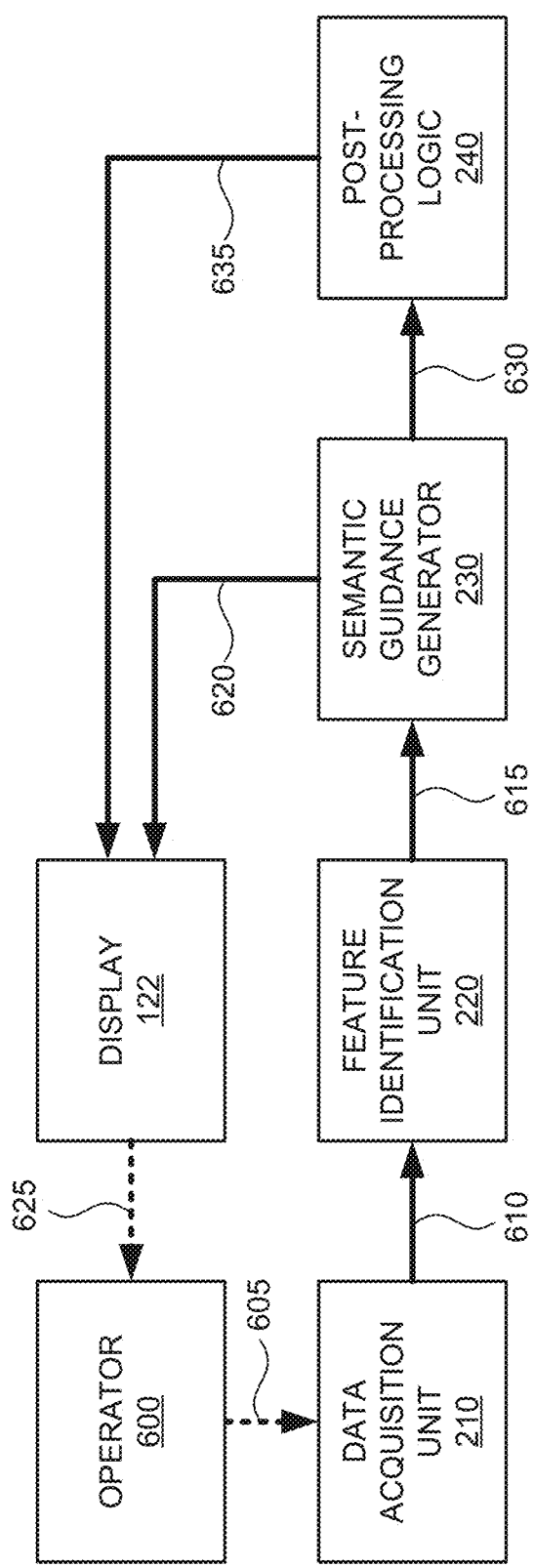
FIG. 6 is a block diagram of exemplary communications for generating real-time semantic feedback in the scanning system of FIGS. 1 and 2.

FIG. 6 is a block diagram of exemplary communications for generating real-time semantic feedback in scanning system 100. An operator 600 may use ultrasound probe 110 to acquire real-time data from a targeted anatomical region. For example, operator 600 may control probe 110 to position 605 the nose of probe 110 toward an organ of interest (e.g., organ 152 of FIG. 1) and emit ultrasonic waves.

Data acquisition unit 210 may receive echo data and process the echo data to generate, for example, a two-dimensional B-mode image 610. Data acquisition unit 210 may forward B-mode image 610 to feature identification unit 220.

Feature identification unit 220 may analyze image 610 using, for example, a multi-class image categorization algorithm to classify image 610 into one or more of multiple different feature categories, such as an image with good quality, an image with strong shadows, an image with reverberations, etc. According to an implementation, image 610 may be simultaneously included in two separate categories. For example, feature identification unit 220 may identify image 610 as having both strong shadows and reverberations. Feature identification unit 220 may forward the category associations 615 for image 610 to semantic guidance generator 230.

Semantic guidance generator 230 may receive category associations 615 and generate semantic-rich guidance based on category associations 615. According to an implementation, semantic guidance generator 230 may match the category association 615 to a particular stored phrase or instruction using a table, such as table 700 described below in connection with FIG. 7.

Figure 7:
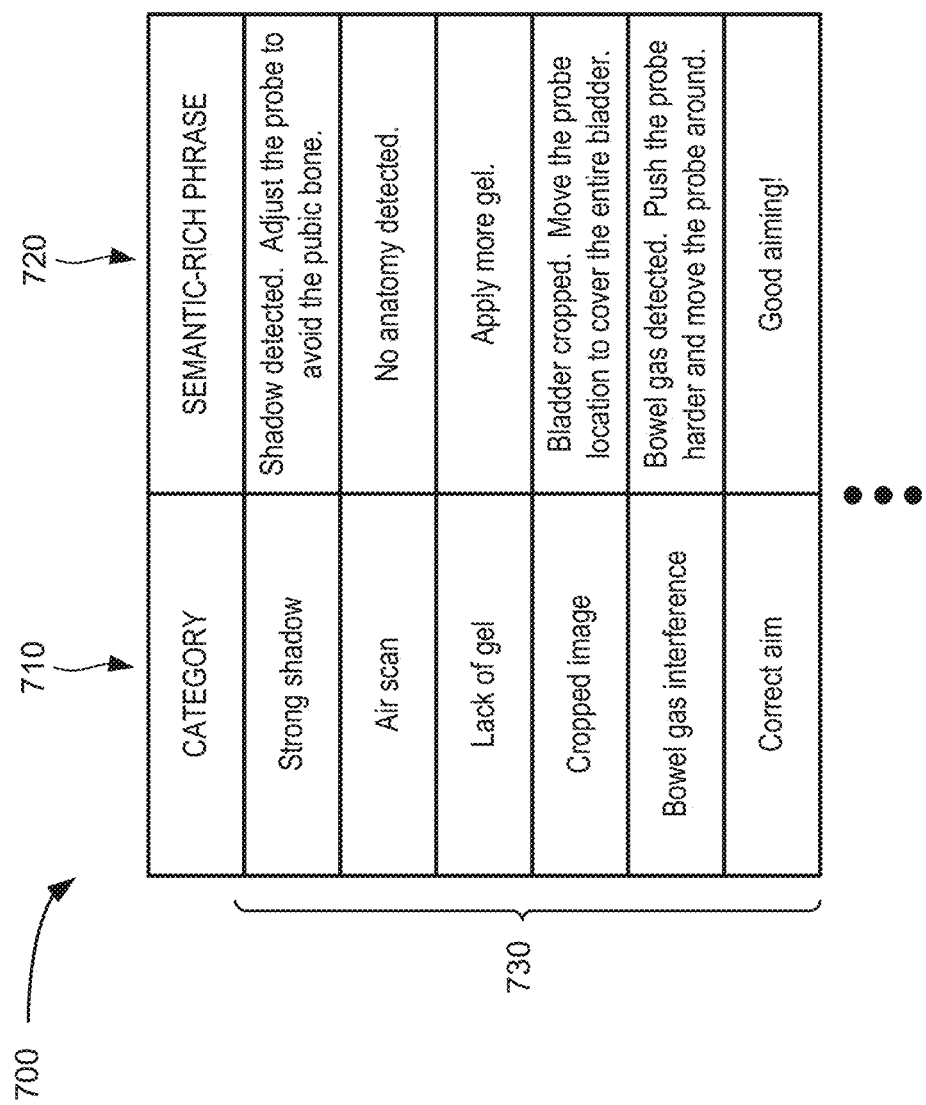
FIG. 7 is an illustration of an exemplary semantic guidance matching table.

FIG. 7 is an illustration of an exemplary semantic guidance matching table 700 that may be used by semantic guidance generator 230. As shown in FIG. 7, semantic guidance matching table 700 may include a category field 710, a semantic-rich phrase field 720, and a variety of entries 730 associated with each of fields 710 and 720.

Category field 710 may include categories for images. Categories may include, for example, categories that indicate machine-detectable features of images 610. Categories in category field 710 may correspond to categories identified by image classifier 420 of feature identification unit 220. For example, categories in category field 710 may include "strong shadow," "air scan," "lack of gel," "cropped image," "bowel gas interference," and "correct aim." Other categories may be used in other implementations, including, for example, direction-oriented subcategories (e.g., "strong shadow—left," "strong shadow—right", etc.).

Semantic-rich phrase field 720 may include text used for visual or audible guidance corresponding to an entry in category field 710. Entries in semantic-rich phrase field 720 may include guidance that an operator may apply to correct aiming of probe 110 and/or improve the quality of image 610. For example, if image 610 is assigned to the "strong shadow" category of category field 710, the corresponding phrase from semantic-rich phrase field 720 may be "Shadow detected. Adjust the probe to avoid the pubic bone." In other implementations, phrase field 720 may include aiming instructions, such as "move the probe left," etc. In other implementations, a bounding box or an indicator may be displayed on screen 122 showing the location of the shadow.

Although FIG. 7 shows exemplary information that may be provided in table 700 for matching semantic guidance to an image category, in other implementations, table 700 may contain less, different, differently-arranged, or additional information than depicted in FIG. 7. For example, in another implementation, table 700 may use different categories for different organs/body areas of interest. Thus, table 700 may include one set of categories and semantic-rich phrases for a bladder scan, while different sets of categories and semantic-rich phrases may be used for a prostate scan, kidney scan, aorta scan, etc. Furthermore, in other implementations, table 700 may be replaced with a flat file structure with strings of features and settings in place of designated fields. In other implementations, the semantic-rich phrases may be automatically generated via the recurrent neural network (RNN), long short-term memory (LSTM), etc. without referring to a fixed table.

Referring again to FIG. 6, semantic guidance generator 230 may select appropriate guidance/text corresponding to the category (e.g., an entry 730 from category field 710) for image 610 and submit guidance 620 (e.g., an entry 730 from semantic-rich phrase field 720) to display 122 for presentation to operator 600. For example, guidance 620 may be presented visibly and/or audibly through display 122 simultaneously with image 610. The semantic-rich guidance may be displayed on the screen or audibly output by a speaker to provide the operator real-time feedback in helping the operator acquire best quality data and subsequently accurate calculated results, such as volume measurements. Because feature identification unit 220 analyzes individual two-dimensional scan images, guidance 620 from semantic guidance generator 230 may be presented (via display 122) in real-time (e.g., less than 0.2 seconds delay). In contrast, post-scan feedback that relies on analysis of multiple images from different scan planes may require that a user wait more than three seconds to allow an entire scan to finish before receiving feedback. Such a lack of real-time feedback can impair the user experience considerably.

Operator 600 may detect 625 guidance 620 from display 122. Assuming guidance 620 includes instructions to adjust aim or otherwise adjust use of probe 110, operator 600 may re-position 605 probe 110. Data acquisition unit 210 may receive new echo data and process the new echo data to generate another B-mode image 610. Feature identification unit 220 may analyze the image 610 to again provide category associations 615 to semantic guidance generator 230.

Assume that category associations 615 indicate image 610 is a clear image (e.g., corresponding to the "correct aim" entry 730 from category field 710). Semantic guidance generator 230 may forward appropriate guidance 620 (e.g., the "Good aiming!" entry 730 from semantic-rich phrase field 720) to display 122 for presentation to operator 600. Additionally (and preferably simultaneously), semantic guidance generator 230 may forward the clear image 630 to post-processing logic 240. According to another implementation, probe 110 or base unit 120 may include a measurement override option to cause semantic guidance generator 230 to forward any last image 630 to post-processing logic 240 (e.g., an image that is not in the "correct aim" category). A measurement override option may cause base unit 120 to calculate a "best effort" result (e.g., for a bladder volume, aorta size, prostate size, kidney size, etc.) based on one or more images 610 with flaws or errors.

Post-processing logic 240 may receive clear image 630 and subsequent clear images 630, if needed, to provide a desired calculation, such as a bladder volume estimate, based on the clear image 630. Post-processing logic 240 may provide a calculated result 635 to display 122 for presentation to the operator 600.

Figure 8:
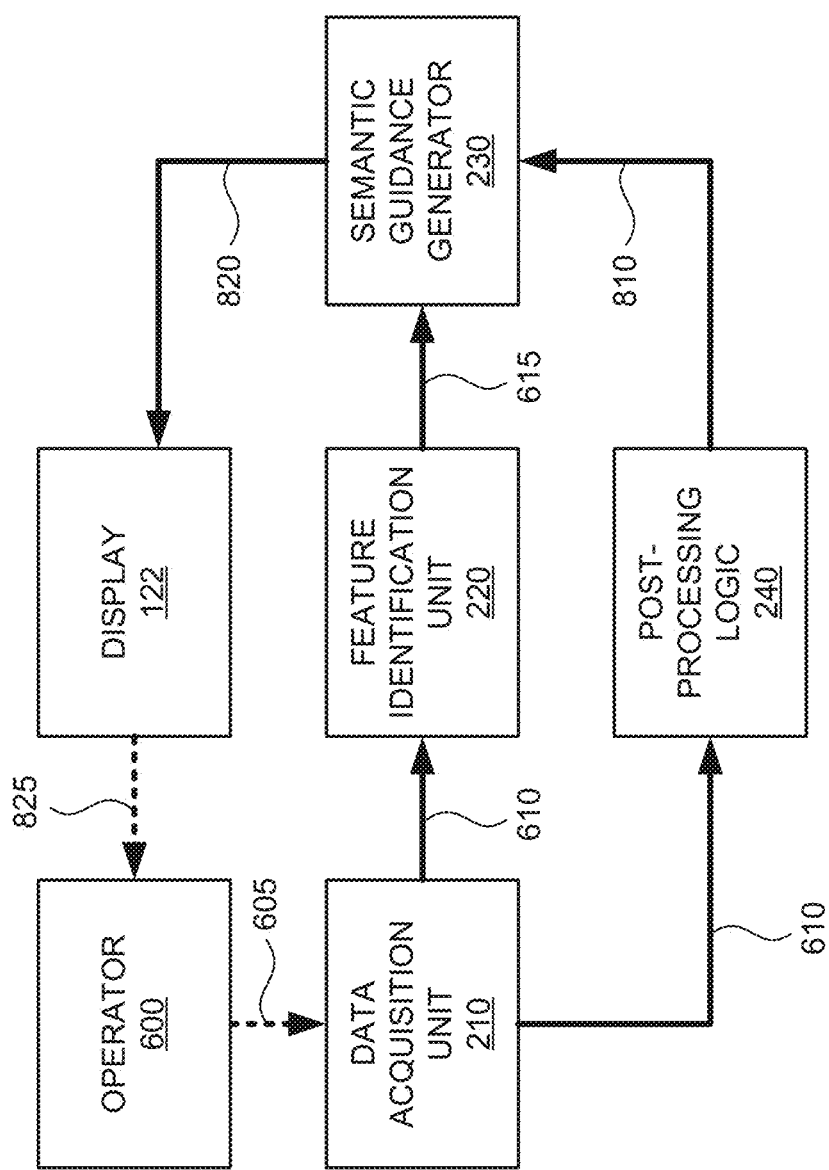
FIG. 8 is a block diagram of exemplary communications for generating real-time semantic feedback in the scanning system of FIGS. 1 and 2, according to another implementation.

FIG. 8 is a block diagram of exemplary communications for generating real-time semantic feedback in scanning system 100 according to another implementation. Communications in FIG. 8 represent feedback provided to an operator along with a requested output.

Similar to communications described in connection with FIG. 6, in FIG. 8, operator 600 may control probe 110 to position 605 the nose of probe 110 toward an organ of interest and emit ultrasonic waves. Data acquisition unit 210 may receive echo data and process the echo data to generate image 610. Data acquisition unit 210 may send image 610 to feature identification unit 220. Feature identification unit 220 may analyze image 610 and classify image 610 into one or more feature categories (e.g., an entry 730 from category field 710). Feature identification unit 220 may provide category associations 615 for image 610 to semantic guidance generator 230.

Additionally (and simultaneously) with sending image 610 to feature identification unit 220, data acquisition unit 210 may send image 610 to post-processing logic 240. Post-processing logic 240 may receive image 610 and subsequent images 610, if needed, to provide a desired calculation, such as a bladder volume estimate, based on image 610. Thus, an image quality assessment (from feature identification unit 220) and a calculated measurement (e.g., bladder volume) can be obtained at the same time. Post-processing logic 240 may provide a calculated result 810 to semantic guidance generator 230.

Semantic guidance generator 230 may receive category associations 615 and calculated results 810. Semantic guidance generator 230 may use category associations 615 and calculated results 810 to generate the post-scan guidance to the operator. For example, semantic guidance generator 230 may use a table similar to table 700 described above, but with different or additional semantic-rich guidance. In one implementation, semantic guidance generator 230 may provide the calculated result 810 with additional guidance to indicate a potential error in a calculated result due to probe aiming or other operator error. Some example guidance may include: "The bladder is not fully covered by the images and in response to determining that the volume could be underestimated;" "There are strong shadows presented in the images and the volume accuracy might be compromised;" "The algorithm has a low level of confidence on the volume reading as there are strong reverberations in images," etc.

Semantic guidance generator 230 may select appropriate guidance/text corresponding to the category for image 610 and submit guidance 820 to display 122 for presentation to operator 600. For example, guidance 820 may be presented visibly and/or audibly through display 122 simultaneously with image 610. Operator 600 may detect 825 guidance 820 on display 122. With the feedback and guidance, operator 600 can choose to rescan the patient or simply accept the result knowing that the calculated results might be less accurate due to the unsatisfied image quality.

Figure 9:
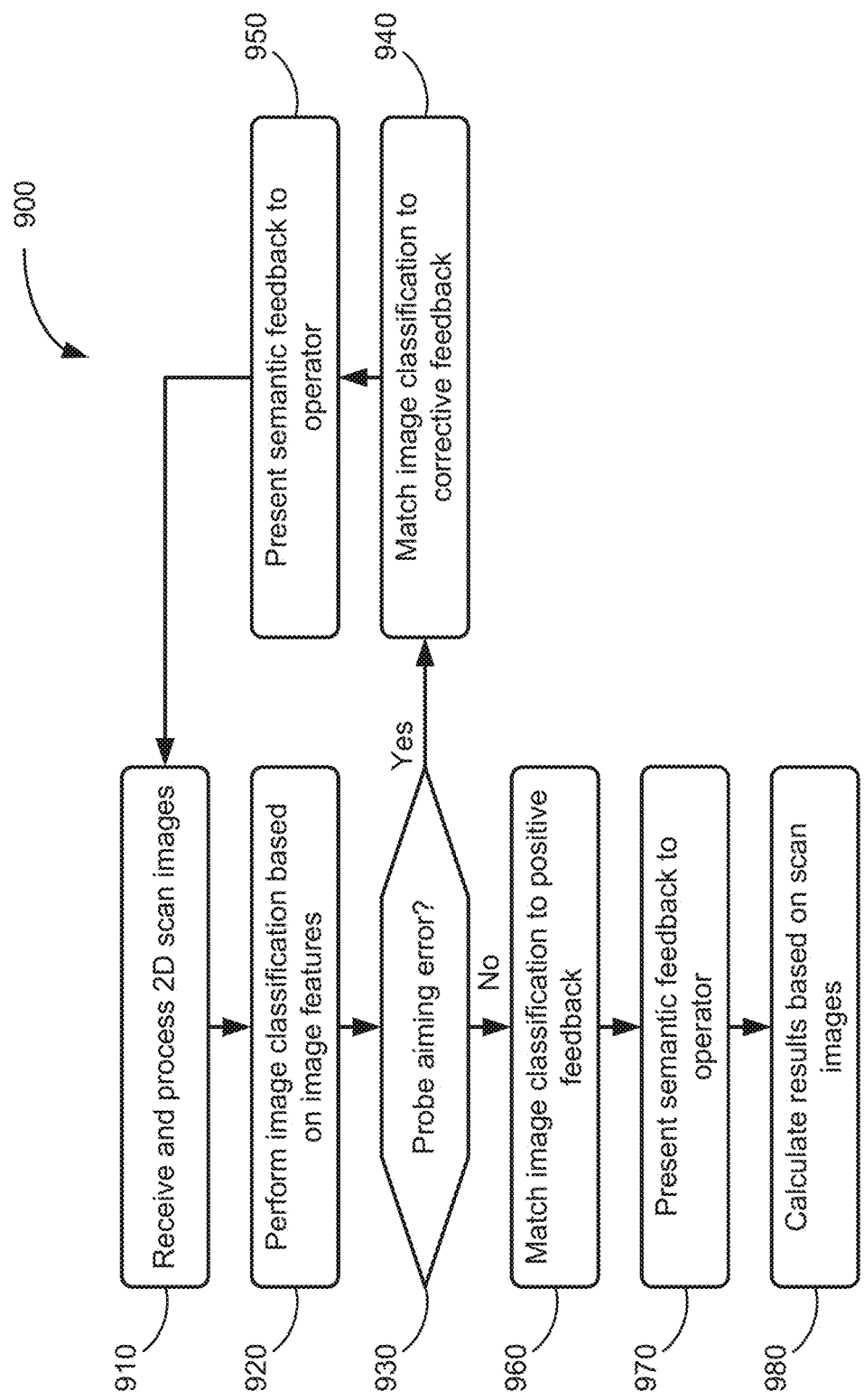
FIG. 9 is a process flow diagram for generating real-time semantic feedback during ultrasound image collection.

FIG. 9 is a flow diagram illustrating exemplary process 900 for providing semantic-rich guidance for ultrasound probe manipulations. Process 900 may be performed, for example, by base unit 120 of system 100. In another implementation, process 900 may be performed by base unit 120 in conjunction with probe 110. In one implementation, process 900 may begin after probe 110 obtains an ultrasound image as described above.

Process 900 may include receiving and processing two-dimensional scan images (block 910). For example, data acquisition unit 210) may receive a B-mode ultrasound image from probe 110 and apply noise reduction and/or other pre-processing techniques to remove speckle and background noise from the image. In some embodiments, the aspect ratio of the raw B-mode image can be adjusted through a resizing process to compensate for differences between axial and lateral resolution. In other implementations, such as bladder scanning applications, a scan conversion can also be applied to make a bladder shape more accurately reflect the actual shape of a typical bladder.

Process 900 may also include performing image classification based on the image features (block 920) and determining if there is probe aiming error based on the image classification (block 930). For example, feature identification unit 220 may receive pre-processed images, such as image 610, from data acquisition unit 210. Feature identification unit 220 may analyze image 610 using, for example, a multi-class image categorization algorithm to classify image 610 into one or more of multiple different feature categories (e.g., strong shadow, cropped image, etc.).

If the image classification indicates there is probe aiming error or other error (block 930—yes), process 900 may include matching the image classification to corrective feedback (block 940), and presenting semantic feedback to the operator (block 950). For example, feature identification unit 220 may forward category associations 615 for image 610 to semantic guidance generator 230. If category associations 615 indicate a feature category indicative of a probe aiming or position error, semantic guidance generator 230 may select appropriate guidance/text corresponding to the category (e.g., an entry 730 from category field 710) for image 610 and submit guidance 620 (e.g., a corrective entry 730 from semantic-rich phrase field 720) to display 122 for presentation to the operator. Process 900 may return to block 910 to receive and process more two-dimensional scan images from probe 110.

If the image classification indicates there is no probe aiming error (block 93013 no), process 900 may include matching the image classification to positive feedback (block 960), presenting semantic feedback to the operator (block 970), and calculating results based on the scan images (block 980). For example, feature identification unit 220 may forward category associations 615 for image 610 to semantic guidance generator 230. If category associations 615 indicate a feature category indicative of a good probe aiming (e.g., entry 730, "correct aim"), semantic guidance generator 230 may select appropriate guidance/text corresponding to the "correct aim" category (e.g., entry 730 "Good aiming!" from semantic-rich phrase field 720) and submit guidance 620 to display 122 for presentation to the operator. Post-processing logic 240 uses clear images 630 to provide a desired calculation, such as a bladder volume estimate, based on the clear images 630, and provide the calculated result 635 for presentation to the operator 600.

Figure 10:
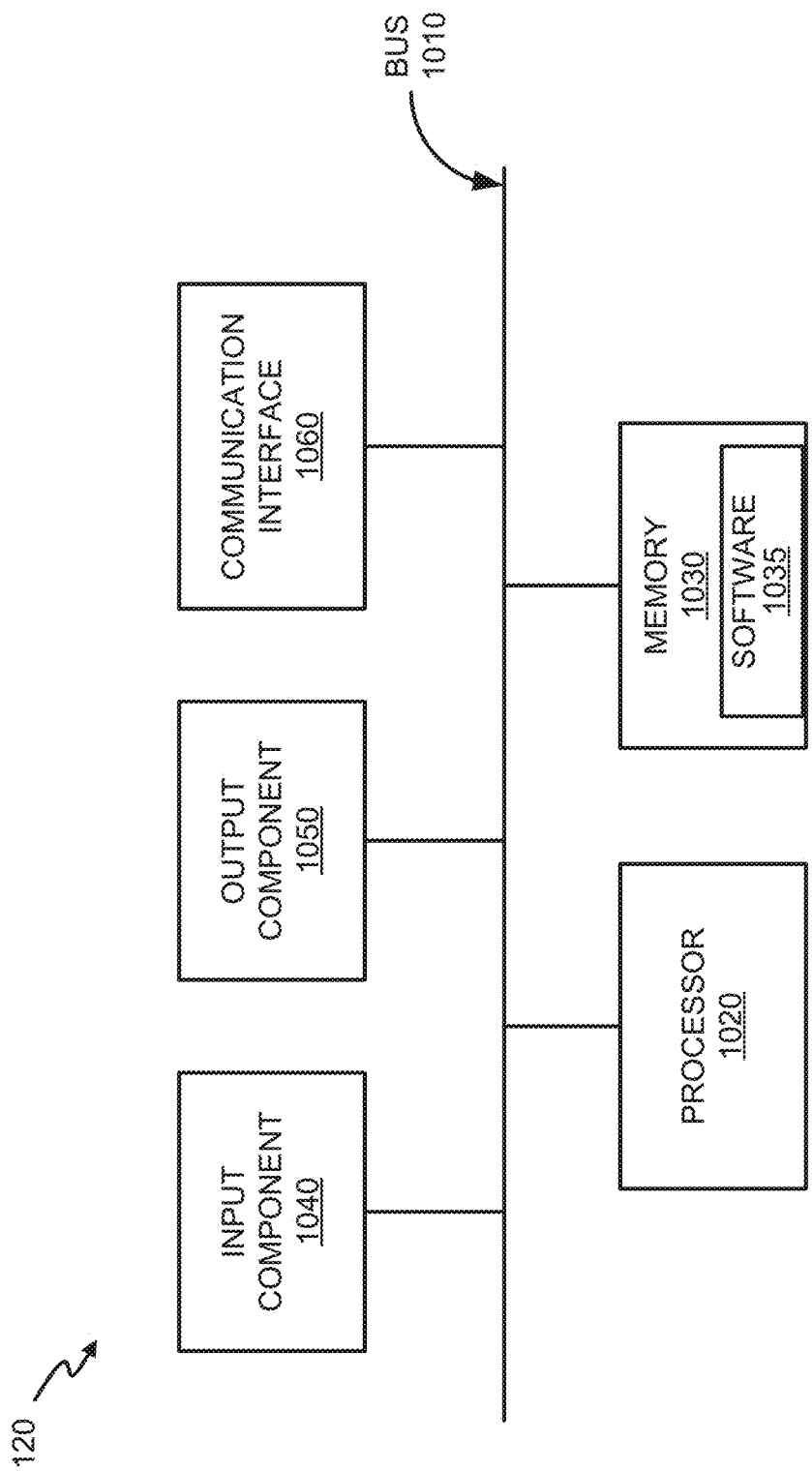
FIG. 10 is a diagram illustrating exemplary components of a base unit in the system of FIG. 1.

FIG. 10 is a diagram illustrating exemplary physical components of base unit 120. Base unit 120 may include a bus 1010, a processor 1020, a memory 1030, an input component 1040, an output component 1050, and a communication interface 1060. In other implementations, probe 110 may include similar components.

Bus 1010 may include a path that permits communication among the components of base unit 120. Processor 1020 may include a processor, microprocessors, ASICs, controllers, programmable logic devices, chipsets, FPGAs, graphics processing unit (GPU), application specific instruction-set processors (ASIPs), system-on-chips (SoCs), central processing units (CPUs) (e.g., one or multiple cores), microcontrollers, and/or some other type of component that interprets and/or executes instructions and/or data. Processor 1020 may be implemented as hardware (e.g., a FPGA, etc.), a combination of hardware and software (e.g., a SoC, an ASIC, etc.), may include one or multiple memories (e.g., cache, etc.), etc.

Memory 1030 may include any type of dynamic storage device that may store information and instructions (e.g., software 1035), for execution by processor 1020, and/or any type of non-volatile storage device that may store information for use by processor 1020.

Software 1035 includes an application or a program that provides a function and/or a process. Software 1035 is also intended to include firmware, middleware, microcode, hardware description language (HDL), and/or other form of instruction.

Input component 1040 may include a mechanism that permits an operator to input information to base unit 120, such as a keyboard, a keypad, a button, a switch, a touch screen, etc. Output component 1050 may include a mechanism that outputs information to the operator, such as a display (e.g., display 122), a speaker, one or more light emitting diodes (LEDs), etc.

Communication interface 1060 may include a transceiver that enables base unit 120 to communicate with other devices and/or systems via wireless communications, wired communications, or a combination of wireless and wired communications. For example, communication interface 1060 may include mechanisms for communicating with another device or system, such as probe 110, via a network, or to other devices/systems, such as a system control computer that monitors operation of multiple base units (e.g., in a hospital or another type of medical monitoring facility). In one implementation, communication interface 1060 may be a logical component that includes input and output ports, input and output systems, and/or other input and output components that facilitate the transmission of data to/from other devices.

Base unit 120 may perform certain operations in response to processor 1020 executing software instructions (e.g., software 1035) contained in a computer-readable medium, such as memory 1030. A computer-readable medium may be defined as a non-transitory memory device. A non-transitory memory device may include memory space within a single physical memory device or spread across multiple physical memory devices. The software instructions may be read into memory 1030 from another computer-readable medium or from another device. The software instructions contained in memory 1030 may cause processor 1020 to perform processes described herein. Alternatively, hardwired circuitry, such as an ASIC, a FPGA, etc., may be used in place of or in combination with software instructions to implement processes described herein. Thus, implementations described herein are not limited to any specific combination of hardware circuitry and software.

Base unit 120 may include fewer components, additional components, different components, and/or differently arranged components than those illustrated in FIG. 10. As an example, base unit 120 may include one or more switch fabrics instead of, or in addition to, bus 1010. Additionally, or alternatively, one or more components of base unit 120 may perform one or more tasks described as being performed by one or more other components of base unit 120.

Systems and methods described herein provide real-time feedback and semantic-rich guidance to operators during the ultrasound scanning. The real-time feedback and semantic-rich guidance is helpful in assisting inexperienced operators to acquire high quality ultrasound data and achieve accurate calculated organ dimensions, such as bladder volume measurements. A deep convolutional neural network enables rapid image classification that can be used to provide real-time feedback.

Systems and methods described herein minimize the requirement for an operator to interpret ultrasound images and transfer that task to logic within system 100. Conventional ultrasound systems require that an operator interpret image content. For inexperienced users, correctly understanding what happens in an ultrasound image is not a trivial task. The systems and methods described herein perform an initial level of image understanding for the operators and provide semantic-rich messages (based on features extracted from the image) to the operators to minimize the burden of image interpretation. By doing so, intra- and inter-operator variability can be minimized and the operator's experience can be improved.

The foregoing description of exemplary implementations provides illustration and description, but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. A method for providing operator guidance during collection of an ultrasound image, the method comprising:
   providing a computing device associated with an ultrasound probe, wherein the computing device is trained via training images to detect pre-identified features from ultrasound images, wherein the pre-identified features include well-identified organs, strong shadows, and cropped organ boundaries;
   receiving, by the computing device, the ultrasound image;
   identifying, by the computing device and based on the pre-identified features, one or more image features of the ultrasound image;
   classifying, by the computing device, the ultrasound image into a category, of multiple stored categories, based on the identified one or more image features, wherein the multiple stored categories include a good category and multiple error categories, and wherein the classifying creates a classified image;
   when the category of the classified image includes one of the multiple error categories:
      selecting, by the computing device, operator guidance corresponding to the category,
      presenting, via one or more of a display and audible sound, the selected operator guidance, and
      receiving, by the computing device, an additional ultrasound image for processing; and
   when the category of the classified image includes the good category, calculating, by the computing device, a result based on a target organ in the classified image.

2. The method of claim 1, wherein the ultrasound image includes a two-dimensional B-mode image.

3. The method of claim 1, wherein the one or more image features include features that are indicative of an improper position or condition of the ultrasound probe.

4. The method of claim 1, wherein the classifying includes using a neural network to perform feature extraction and image classification.

5. The method of claim 1, wherein, in response to receiving the additional ultrasound image, the method further comprises:
   identifying, by the computing device in real time, one or more image features of the additional ultrasound image.

6. The method of claim 1, wherein the operator guidance further comprises an indication of a potential error in the classified image.

7. The method of claim 1, wherein the result includes an organ dimension.

8. The method of claim 1, wherein the target organ includes a bladder.

9. The method of claim 1, wherein the computing device includes one of a field-programmable gate array (FPGA) or an application specific integrated circuit (ASIC) to classify the ultrasound image using a multi-class image categorization algorithm.

10. The method of claim 1, wherein the pre-identified features further include:

bowel gas interference,
a lack of detectable anatomy, and
reverberation.

11. The method of claim 1, wherein the operator guidance indicates an image feature identification and a corrective operator action.

12. A device, comprising:
a memory device for storing instructions; and
a processor configured to:
   train, via training images, the device to detect pre-identified features from ultrasound images, wherein the pre-identified features include well-identified organs, strong shadows, and cropped organ boundaries,
   receive an ultrasound image,
   identify, based on the pre-identified features, one or more image features of the ultrasound image,
   classify the ultrasound image into a category, of multiple stored categories, based on the identified one or more image features,
      wherein the multiple stored categories include a good category and multiple error categories, and
      wherein the classifying creates a classified image,
   when the category of the classified image includes one of the multiple error categories:
      select operator guidance corresponding to the category,
      present, via one or more of a display and audible sound, the selected operator guidance, and
      receive an additional ultrasound image for processing, and
   when the category of the classified image includes the good category, calculate a result based on a target organ in the classified image.

13. The device of claim 12, wherein the ultrasound image includes a two-dimensional scan image.

14. The device of claim 12, wherein the device includes an ultrasound probe, and wherein the one or more image features include features that are indicative of an improper position or condition of the ultrasound probe.

15. The device of claim 12, wherein the memory device is further configured to store a pre-trained model.

16. The device of claim 15, wherein, when classifying the ultrasound image, the processor is further configured to:
   apply a neural network to extract and match the one or more image features of the ultrasound image with the pre-trained model for classification.

17. The device of claim 12, wherein the pre-identified features further includes:
   a lack of detectable anatomy.

18. The device of claim 12, wherein, the processor is further configured to:
   select positive operator feedback when the classified image provides an acceptable representation of the target organ, and
   present, via the display, the positive operator feedback.

19. A non-transitory computer-readable medium storing instructions executable by at least one processor of a device, which when executed cause the device to:
   train, via training images, the device to detect pre-identified features from ultrasound images, wherein the pre-identified features include well-identified organs, strong shadows, and cropped organ boundaries;
   receive an ultrasound image;
   identify, based on the pre-identified features, one or more image features of the ultrasound image;
   classify the ultrasound image into a category, of multiple stored categories, based on the identified one or more image features,
      wherein the multiple stored categories include a good category and multiple error categories, and
      wherein the classifying creates a classified image;
   when the category of the classified image includes one of the multiple error categories:
      select operator guidance corresponding to the category,
      present, via one or more of a display and audible sound, the selected operator guidance, and
      receive an additional ultrasound image for processing; and
   when the category of the classified image includes the good category, calculate a result based on a target organ in the classified image.

20. The non-transitory computer-readable medium claim 19, wherein the instructions to classify further comprise one or more instructions to:
   apply a neural network to extract and match features of the ultrasound image with a pre-trained model for classification.

* * * * *